(12) United States Patent
Müller et al.

(10) Patent No.: US 6,432,965 B1
(45) Date of Patent: Aug. 13, 2002

(54) FUNGICIDAL COMBINATIONS COMPRISING THIENO(2,3-D)PYRIMIDIN-4-ONE

(75) Inventors: Kaspar Müller, Schönenbuch (CH); Gertrude Knauf-Beiter, Müllheim; Dietrich Hermann, Wittlingen, both of (DE); Harald Walter, Rodersdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/555,444

(22) Filed: Sep. 15, 2000

(51) Int. Cl.$^7$ ............... A01N 43/54; A01N 43/36
(52) U.S. Cl. ............ 514/258; 514/422; 514/427
(58) Field of Search ............... 514/258, 427, 514/422

(56) References Cited

FOREIGN PATENT DOCUMENTS

| WO | WO97/02262 | 1/1997 |
|----|-----------|--------|
| WO | WO97/33890 | 9/1997 |

*Primary Examiner*—Allen J. Robinson
(74) *Attorney, Agent, or Firm*—William A. Teoli, Jr.; Thomas Hamilton

(57) ABSTRACT

The invention relates to novel fungicidal compositions having a synergistically increased action, wherein component a) is a thieno[2,3-d]pyrimidin-4-one of formula I

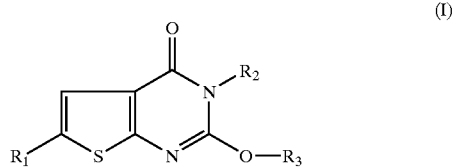

wherein $R_1$ is halogen, $R_2$ is $C_1$–$C_5$alkyl, —$CH_2$-cyclopropyl and $R_3$ is $C_1$–$C_5$alkyl, —$CH_2$-cyclopropyl; in association with b) either an anilinopyrimidine fungicide (II), or an azole fungicide (III), or a morpholine fungicide (IV), or a strobilurin compound (V), or a pyrrole compound (VI), or a phenylamide (VII), or a dithiocarbamate fungicide selected from mancozeb, maneb, metiram and zineb, or a copper compound selected from copper hydroxide, coopper oxychloride, copper sulfate and oxine-copper, or a phthalimide compound (VIII), or prochloraz, or triflumizole, or pyrifenox, or acibenzolar-S-methyl, or chlorothalonil, or cymoxanil, or dimethomorph, or famoxadone, or fenhexamide, or fenarimol, or fluazinam, or fosetyl-aluminium, orquinoxyfen, or fenpropidine, or spiroxamine, or carbendazime, or thlabendazole, or ethirimol, or triazoxide, or guazatine.

7 Claims, No Drawings

FUNGICIDAL COMBINATIONS COMPRISING THIENO(2,3-D)PYRIMIDIN-4-ONE

This application is a 371 of PCT/EP98/07677, filed Nov. 27, 1998.

The present invention relates to novel fungicidal compositions for the treatment of phytopathogenic diseases of crop plants and against infestation on propagation stock of plants or on other vegetable material, especially phytopathogenic fungi, and to a method of combating phytopathogenic diseases on crop plants or for seed dressing.

It is known that certain pyrimidin-4-one derivatives have biological activity against phytopathogenic fungi, e.g. known from WO 97/33890 where their properties and methods of preparation are described. On the other hand anilinopyrimidines, azole fungicides, phthalimides, phenylamides, strobilurines, pyrroles, dithiocarbamates and morpholines are widely known as plant fungicides for application in various crops of cultivated plants. However, crop tolerance and activity against phytopathogenic plant fungi do not always satisfy the needs of agricultural practice in many incidents and aspects.

It has now been found that the use of a) a thieno[2.3-d]pyrimidin-4-one of formula I

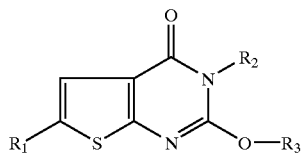
(I)

wherein
$R_1$ is halogen,
$R_2$ is $C_1$–$C_5$alkyl, —$CH_2$-cyclopropyl and
$R_3$ is $C_1$–$C_5$alkyl, —$CH_2$-cyclopropyl;
in association with b) either an anilinopyrimidine of formula II

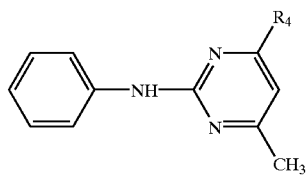
(II)

wherein
$R_4$ is methyl, 1-propynyl or cyclopropyl;
or an azole of formula III

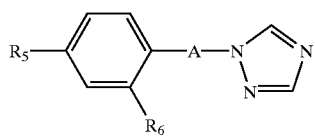
(III)

wherein
A is selected from

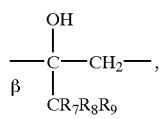 (i)

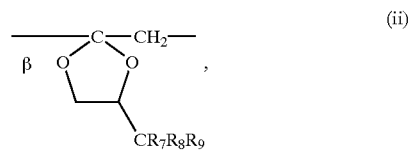 (ii)

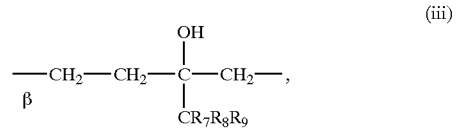 (iii)

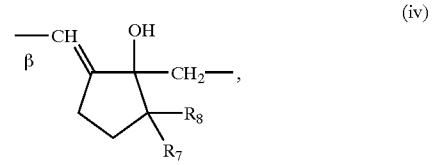 (iv)

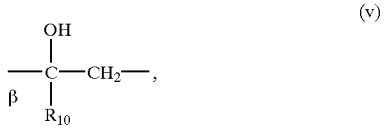 (v)

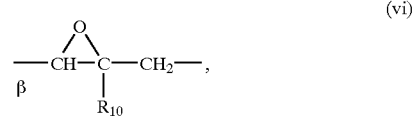 (vi)

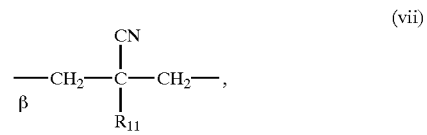 (vii)

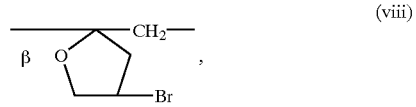 (viii)

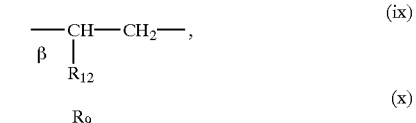 (ix)

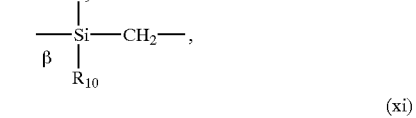 (x)

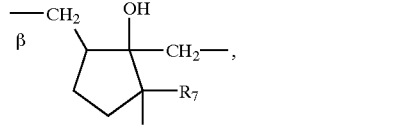 (xi)

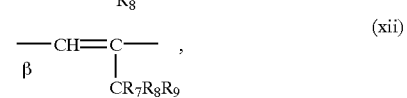 (xii)

-continued

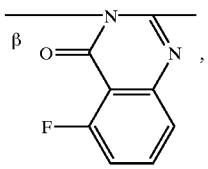
(xiii)

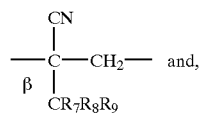
(xiv)

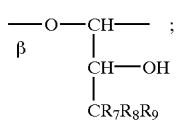
(xv)

whereby the β-carbon attaches to benzene ring of formula III, and wherein $R_5$ is H, F, Cl, phenyl, 4-fluorophenoxy or 4-chlorophenoxy;

$R_6$ is H, Cl or F;

$R_7$ and $R_8$ are independently H or $CH_3$;

$R_9$ is $C_{1-4}$alkyl or cyclopropyl;

$R_{10}$ is 4-chlorophenyl or 4-fluorophenyl;

$R_{11}$ is phenyl, and $R_{12}$ is allyloxy, $C_{1-4}$alkyl, or 1,1,2,2-tetrafluoroethoxy-methyl, and the salts of such azole fungicide;

or a morpholine fungicide of formula IV

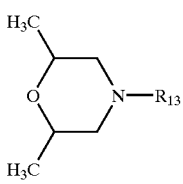
(IV)

wherein $R_{13}$ is $C_{8-15}$cycloalkyl, $C_{8-15}$alkyl, or $C_{1-4}$alkylphenyl-$C_{1-4}$alkyl, and the salts of such morpholine fungicide;

or a strobilurin compound of formula V

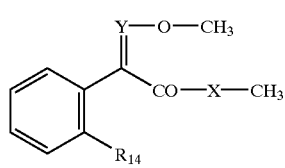
(V)

wherein

X is NH or O,

Y is CH or N, and $R_{14}$ is 2-methylphenoxy-methyl, 2,5-dimethylphenoxy-methyl, 4-(2-cyanophenoxy)-pyrimidin-6-yloxy, or 4-(3-trifluoromethylphenyl)-3-aza-2-oxa-3-pentenyl;

or a pyrrole compound of the formula VI

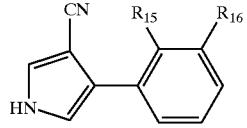
(VI)

wherein $R_{15}$ and $R_{16}$ are indendently halo, or together from a perhalomethylendioxo bridge; or a phenylamide of the formula VII

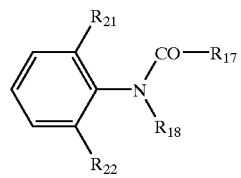
(VII)

wherein $R_{17}$ is benzyl, methoxymethyl, 2-furanyl, chloromethyl or

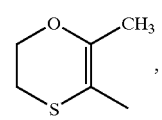

$R_{18}$ is 1-methoxycarbonyl-ethyl, or

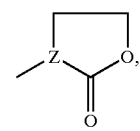

Z is CH or N, $R_{21}$ is hydrogen or methyl, $R_{22}$ is hydrogen or methyl;

or a dithiocarbamate fungicide selected from mancozeb, maneb, metiram and zineb; or a copper compound selected from copper hydroxide, copper oxychloride, copper sulfate and oxine-copper;

or sulfur;

or a phthalimide compound of the formula VIII

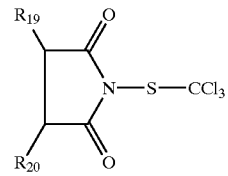
(VIII)

wherein $R_{19}$ and $R_{20}$ together form a 4-membered bridge $-CH_2-CH=CH-CH_2-$ or $=CH-CH=CH-CH=$;

or with compound of formula IX
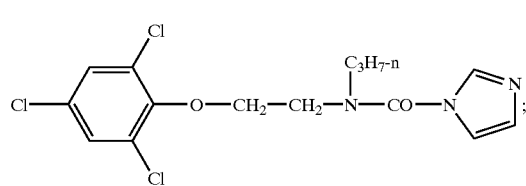
or with a compound of formula X
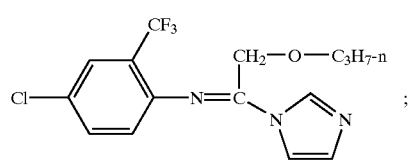
or with a compound of formula XI
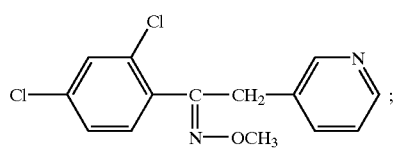
or with a compound of formula XII
or with a compound of formula XIII
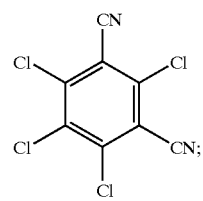
or with a compound of formula XIV
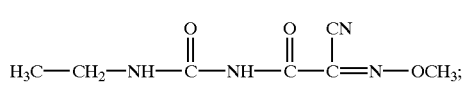
or with a compound of formula XV
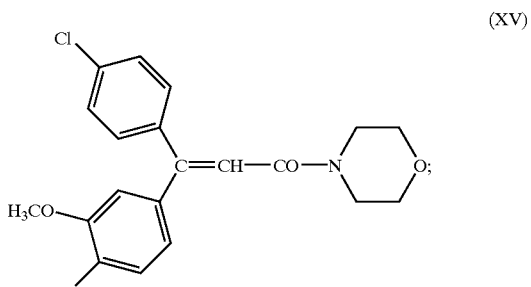
or with a compound of formula XVI
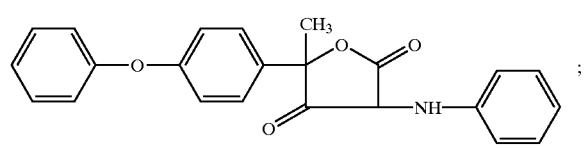
or with a compound of formula XVII
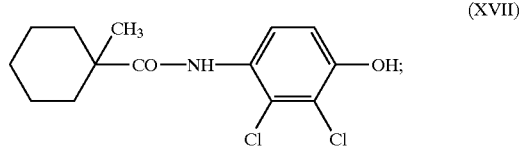
or with a compound of formula XVIII
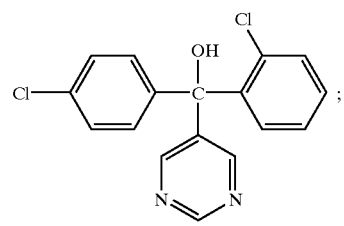
or with a compound of formula XIX
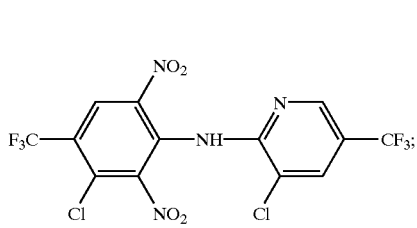

or with a compound of formula XX

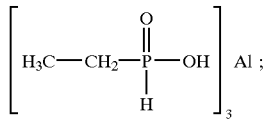
(XX)

or with a compound of formula XXI

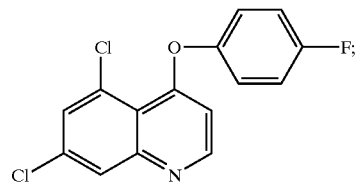
(XXI)

or with a compound of formula XXII

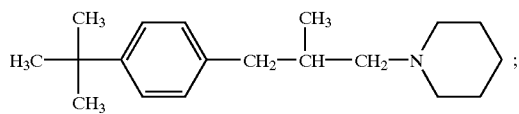
(XXII)

or with a compound of formula XXIII

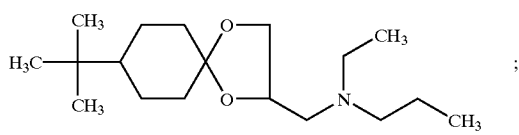
(XXIII)

or with a compound of formula XXIV

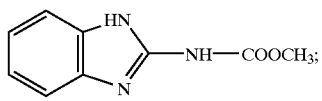
(XXIV)

or with a compound of formula XXV

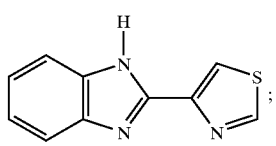
(XXV)

or with a compound of formula XXVI

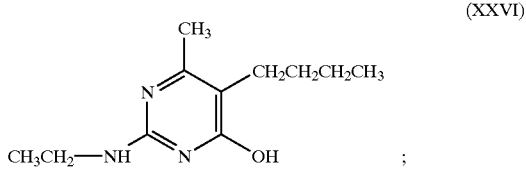
(XXVI)

or with a compound of formula XXVII

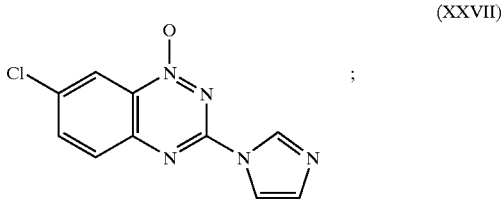
(XXVII)

or with a compound of formula XXVIII

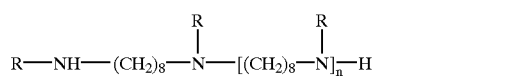
(XXVIII)

wherein n is 0 or 1 or 2 etc, and

R is hydrogen or —C(=NH)NH$_2$;

is particularly effective in combating or preventing fungal diseases of crop plants. These combinations exhibit synergistic fungicidal activity.

The combinations according to the invention may also comprise more than one of the active components b), if broadening of the spectrum of disease control is desired. For instance, it may be advantageous in the agricultural practice to combine two or three components b) with the any of the compounds of formula I, or with any preferred member of the group of compounds of formula I. From WO 97/33890 the following specific species of formula I are known:

| Compound No. | R$_1$ | R$_2$ | R$_3$ |
|---|---|---|---|
| I.01 | Cl | n-propyl | n-propyl |
| I.02 | Br | n-propyl | n-propyl |
| I.03 | Cl | n-propyl | n-butyl |
| I.04 | Br | n-propyl | n-butyl |
| I.05 | Cl | n-butyl | n-propyl |
| I.06 | Br | n-butyl | n-propyl |
| I.07 | Cl | i-butyl | n-propyl |
| I.08 | Br | i-butyl | n-propyl |
| I.09 | Cl | n-propyl | i-butyl |
| I.10 | Br | n-propyl | i-butyl |

A preferred embodiment of the present invention is represented by those combinations which comprise as component a) a compound of the formula I wherein R$_1$ is chloro or bromo and R$_2$ is n-propyl, n-butyl, i-butyl and R$_3$ is n-propyl, n-butyl, i-butyl.

Among the mixtures of present invention most preference is given to the mixture of compounds I.01, I.02, I.03, I.04, I.05, I.06,I.07 or I.08 with the compounds of component b), especially the commercially available products falling within the given ranges, i.e. the commercial products mentioned throughout this document.

Salts of the azole, amine and morpholine active ingredients are prepared by reaction with acids, e.g., hydrohalo acids such as hydrofluoric acid, hydrochloric acid, hydrobromic acid and hydroiodic acid, or sulfuric acid, phosphoric acid or nitric acid, or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzensulfonic acid, p-toluenesulfonic acid, methanesulfonic acid, salicylic acid, p-aminosalicylic acid and 1,2-naphtalenedisulfonic acid.

The active ingredient combinations are effective against phytopathogenic fungi belonging to the following classes: Ascomycetes (e.g. Venturia, Podosphaera, Erysiphe, Monilinia, Sclerotinia, Mycosphaerella, Uncinula); Basidiomycetes (e.g. the genus Hemileia, Rhizoctonia, Tilletia, Puccinia); Fungi imperfecti (e.g. Botrytis, Helminthosporium, Rhynchosporium, Fusarium, Septoria, Cercospora, Alternaria, Pyricularia and Pseudocercosporella herpotrichoides); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts): cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers) and their seeds. This list does not represent any limitation.

The combinations of the present invention may also be used in the area of protecting technical material against attack of fungi. Technical areas include wood, paper, leather, constructions, cooling and heating systems, ventilation and air conditioning systems, and the like. The combinations according the present invention can prevent the disadvantageous effects such as decay, discoloration or mold.

The combinations according to the present invention are particularly effective against powdery mildews and rusts, pyrenophora, rhynchosporium and leptosphaeria fungi, in particular against pathogens of monocotyledonous plants such as cereals, including wheat and barley. They are furthermore particularly effective against downy mildew species, especially against plasmopara in vine.

The amount of combination of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

Particularly preferred mixing partners of the compounds of formula II are those in which $R_4$ is methyl or cyclopropyl. These compounds are commonly known as pyrimethanil and cyprodinil.

Particularly preferred mixing partners of the compounds of formula III are those in which $R_5$ is Cl, $R_6$ and $R_7$ are H, $R_8$ is $CH_3$ and $R_9$ is cyclopropyl and A is the moiety (i) (commonly known as cyproconazole); those wherein $R_5$ and $R_6$ are Cl, $R_7$ and $R_8$ are H, $R_9$ is propyl and A is the moiety (i) (commonly known as hexaconazole); those in which $R_5$ is 4-chlorophenoxy, $R_6$ is Cl, $R_7$, $R_8$ and $R_9$ are H and A is the moiety (ii) (commonly known as difenoconazole); those in which $R_5$ and $R_6$ are Cl, $R_7$ and $R_8$ are H, $R_9$ is ethyl and A is the moiety (ii) (commonly known as etaconazole); those in which $R_5$ and $R_6$ are Cl, $R_7$ and $R_8$ are H, $R_9$ is propyl and A is the moiety (ii) (commonly known as propiconazole); those in which $R_5$ is Cl, $R_6$ is H, $R_7$, $R_8$ and $R_9$ are $CH_3$ and A is the moiety (iii) (commonly known as tebuconazole); those in which $R_5$ is Cl, $R_6$ is H and A is the moiety (iv) (commonly known as triticonazole); those in which $R_5$ is H, $R_6$ is F, $R_{10}$ is 4-fluorophenyl and A is the moiety (v) (commonly known as flutriafol); those in which $R_5$ is H, $R_6$ is Cl, $R_{10}$ is 4-fluorophenyl and A is the moiety (vi) (commonly known as epoxiconazole); those in which $R_5$ is Cl, $R_6$ is H, $R_{11}$, is phenyl and A is the moiety (vii) (commonly known as fenbuconazole); those in which $R_5$ and $R_6$ are Cl, and A is the moiety (viii) (commonly known as bromuconazole); those in which $R_5$ and $R_6$ are Cl, $R_{12}$ is propyl and A is the moiety (ix) (commonly known as penconazole); those in which $R_5$ and $R_6$ are Cl, $R_{12}$ is allyloxy and A is the moiety (ix) (commonly known as imazalil); those in which $R_5$ and $R_6$ are Cl, $R_{12}$ is 1,1,2,2-tetrafluoroethoxymethyl and A is the moiety (ix) (commonly known as tetraconazole); those wherein $R_5$ is F, $R_6$ is H, $R_9$ is $CH_3$, $R_{10}$ is 4-fluorophenyl, and A is the moiety (x) (commonly known as flusilazole); those in which $R_5$ is chloro, $R_6$ is hydrogen, $R_7$ and $R_8$ are methyl and A is the moiety (xi) (commonly known as metconazole); those wherein $R_5$ and $R_6$ are chloro, $R_7$ and $R_8$ are H, $R_9$ is t-butyl and A is the moiety (xii) (commonly known as diniconazole); those wherein $R_5$ and $R_6$ are chloro and A is the moiety (xiii) (commonly known as fluquinconazole); those wherein $R_5$ is chloro, $R_6$, $R_7$ and $R_8$ are H, $R_9$ is n-butyl and A is the moiety (xiv) (commonly known as myclobutanil); those wherein $R_5$ is chloro, $R_6$ is H, $R_7$, $R_8$ and $R_9$ are methyl and A is the moiety (xv) (commonly known as triadimenol); and those wherein $R_5$ is phenyl, $R_7$,$R_8$ and $R_9$ are methyl and A is the moiety (xv) (commonly known as bitertanol).

Particularly preferred mixing partners of the compounds of formula IV are those wherein $R_{13}$ is cyclododecyl (commonly known as dodemorph), or $C_{10-13}$alkyl (commonly known as tridemorph), or 3-(4-tert-butylphenyl)-2-methylpropyl (commonly known as fenpropimorph). Predominantly, the cis-positioning of the methyl groups at the morpholine ring is present in the compounds of formula IV when used in the combinations of the invention.

Particularly preferred mixing partners of the compounds of formula V are those wherein X and Y are O, and $R_{14}$ is 2-methylphenoxy-methyl (commonly known as kresoxim-methyl): or wherein X is NH, Y is N and $R_{14}$ is 2,5-dimethylphenoxy-methyl; or wherein X is O, Y is CH and $R_{14}$ is 4-(2-cyanophenoxy)-pyrimidin-6-yloxy (commonly known as azoxystrobin), or wherein X is O, Y is N and $R_{14}$ is 4-(3-trifluoromethylphenyl)-3-aza-2-oxa-3-pentenyl.

Particularly preferred mixing partners of the compounds of formula VI are those wherein $R_{15}$ and $R_{16}$ are both chloro (commonly known as fenpiclonil); or wherein $R_{15}$ and $R_{16}$ together form a bridge —O—$CF_2$—O— (commonly known as fludioxonil).

Particularly preferred mixing partners of the compounds of formula VII are those wherein $R_{17}$ is benzyl, $R_{21}$ and $R_{22}$ are methyl and $R_{18}$ is 1-methoxycarbonyl-ethyl (commonly known as benalaxyl); or wherein $R_{17}$ is 2-furanyl, $R_{21}$ and $R_{22}$ are methyl and $R_{18}$ is 1-methoxycarbonyl-ethyl (commonly known as furataxyl); or wherein $R_{17}$ is methoxymethyl, $R_{21}$ and $R_{22}$ are methyl and $R_{18}$ is 1-methoxycarbonyl-ethyl or is (R)-1-methoxycarbonyl-ethyl (commonly known as metalaxyl and R-metalaxyl); or wherein $R_{17}$ is chloromethyl, $R_{21}$ and $R_{22}$ are methyl and $R_{18}$ is

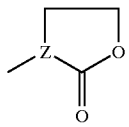

whereby Z is CH (commonly known as orfurace); or wherein $R_{17}$ is methoxymethyl, $R_{21}$ and $R_{22}$ are methyl and $R_{18}$ is

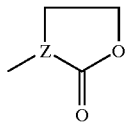

whereby Z is N (commonly known as oxadixyl); or wherein $R_{17}$ is

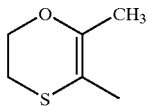

and $R_{18}$, $R_{21}$ and $R_{22}$ is hydrogen (commonly known as carboxin).

Particularly preferred mixing partners of the compounds of formula VIII are those wherein $R_{19}$ and $R_{20}$ together form the bridge —CH$_2$—CH═CH—CH$_2$— (commonly known as captan); or wherein $R_{19}$ and $R_{20}$ together form the bridge ═CH—CH═CH—CH═ (commonly known as folpet).

The compound of formula IX is commonly known as prochloraz.

The compound of formula X is commonly known as triflumizole.

The compound of formula XI is commonly known as pyrifenox.

The compound of formula XII is commonly known as acibenzolar-S-methyl.

The compound of formula XIII is commonly known as chlorothalonil.

The compound of formula XIV is commonly known as cymoxanil.

The compound of formula XV is commonly known as dimethomorph.

The compound of formula XVI is commonly known as famoxadone.

The compound of formula XVII is commonly known as fenhexamide.

The compound of formula XVIII is commonly known as fenarimol.

The compound of formula XIX is commonly known as fluazinam.

The compound of formula XX is commonly known as fosetyl-aluminium.

The compound of formula XXI is commonly known as quinoxyfen.

The compound of formula XXII is commonly known as fenpropidine.

The compound of formula XXIII is commonly known as spiroxamine.

The compound of formula XXIV is commonly known as carbendazime.

The compound of formula XXV is commonly known as thiabendazole.

The compound of formula XXVI is commonly known as ethirimol.

The compound of formula XXVII is commonly known as triazoxide.

The compound of formula XXVIII is commonly known as guazatine.

The specific compounds b) mentioned in the preceding paragraphs are commercially available. Other compounds failing under the scope of the various groups of component b) are obtainable according to procedures analogous to those known for preparing the commercially available compounds.

It has been found that the use of compounds of formulae XI to XXVIII in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely, Specific preferred mixtures according to the present invention are understood to be represented by the combinations of active ingredients of formula I, or any of the subgroups of formula I, or specifically mentioned members of the subgroups with a second fungicide selected from the group comprising pyrimethanil, cyprodinil, cyproconazole, hexaconazole, difenoconazole, etaconazole, propiconazole, tebuconazole, triticonazole, flutriafol, epoxiconazole, fenbuconazole, bromuconazole, penconazole, imazalil, tetraconazole, flusilazole, metconazole, diniconazole, fluquinconazole, myclobutanil, triadimenol, bitertanol, dodemorph, tridemorph, fenpropimorph, mancozeb, maneb, metiram, zineb, copper hydroxide, copper oxychloride, copper sulfate, oxine-copper, sulfur, kresoxim-methyl, azoxystrobin, 2-[2-(2,5-dimethylphenoxy-methyl)-phenyl]-2-methoximino-acetic acid N-methyl-amide, methyl 2-{2-[4-(3-trifluoromethylphenyl)-3-aza-2-oxa-3-pentenyl]-phenyl}-2-methoxyimino-acetate, fenpiclonil, fludioxonil, benalaxyl, furalaxyl, metalaxyl, R-metalaxyl, orfurace, oxadixyl, carboxin, captan, folpet, prochloraz, triflumizole, pyrifenox, acibenzolar-S-methyl, chlorothalonil, cymoxanil, dimethomorph, famoxadone, fenhexamide, fenarimol, fluazinam, fosetyl-aluminium, quinoxyfen, fenpropidine, spiroxamine, carbendazime, thiabendazol, ethirimol, triazoxide and guazatine.

From this group a subgroup b1 is preferred comprising combinations with cyproconazole, hexaconazole, difenoconazole, propiconazole, tebuconazole, flutriafol, epoxiconazole, fenbuconazole, bromuconazole, penconazole, tetraconazole, flusilazole, metconazole, diniconazole, triadimenol, fluquinconazole and prochloraz.

From this group combinations with propiconazole, difenoconazole, penconazole, tebuconazole, prochloraz, epoxiconazole and cyproconazole are of particular interest as preferred embodiments of this invention as subgroup b1a.

A further preferred subgroup b2 comprises combinations with cyprodinil, tridemorph, fenpropimorph, kresoxim-methyl, azoxystrobin, methyl 2-{2-[4-(3- trifluoromethylphenyl)-3-aza-2-oxa-3-pentenyl]-phenyl}-2-methoxyimino-acetate, acibenzolar-S-methyl, chlorothaionil, famoxadone, quinoxyfen, fenpropidine and carbendazime.

From this group combinations with cyprodinil, fenpropimorph, kresoxim-methyl, azoxystrobin, methyl 2-{2-[4-(3-trifluoromethylphenyl)-3-aza-2-oxagentenyl]-phenyl}2-methoxyimino-acetate, acibenzolar-S-methyl and fenpropidine are of particular interest as preferred embodiments of this invention as subgroup b2a.

Further combinations of interest are the following:

compound I.01 with any member of groups b1 and b2, or with any member of groups b1a and b2a;

compound I.02 with any member of groups b1 and b2, or with any member of groups b1a and b2a;

compound I.03 with any member of groups b1 and b2, or with any member of groups b1a and b2a;

compound I.04 with any member of groups b1 and b2, or with any member of groups b1a and b2a.

compound I.05 with any member of groups b1and b2, or with any member of groups b1a and b2a;

compound I.06 with any member of groups b1and b2, or with any member of groups b1a and b2a;

compound I.07 with any member of groups b1and b2, or with any member of groups b1a and b2a;

compound I.08 with any member of groups b1 and b2, or with any member of groups b1a and b2a.

The weight ratio of a):b) is so selected as to give a synergistic fungicidal action. In general the weight ratio of a):b) is between 100:1 and 1:400. The synergistic action of the composition is apparent from the fact that the fungicidal action of the composition of a)+b) is greater than the sum of the fungicidal actions of a) and b).

Where the component b) is an anilinopyrimidine of formula II the weight ratio of a):b) is for example between 1:2 and 1:36, especially 1:2 and 1:18, and more preferably 1:3 and 1:8.

Where the component b) is an azole fungicide of formula III the weight ratio of a):b) is for example between 10:1 and 1:20, especially 5:1 and 1:10, and more preferably 2:1 and 1:4.

Where component b) is a morpholine fungicide of formula IV, the weight ratio of a):b) is for example between 1:2 and 1:30, especially 1:3 and 1:15, and more preferably 1:3 and 1:10.

Where component b) is a strobilurin fungicide of formula V, the weight ratio of a):b) is for example between 2:1 and 1:10, especially 1:1 and 1:8, and more preferably 1:2 and 1:5.

Where component b) is a pyrrole fungicide of formula VI, the weight ratio of a):b) is for example between 1:3 and 1:30, especially 1:1.5 and 1:7, and more preferably 1:2 and 1:5.

Where component b) is a phenylamide fungicide of formula VII, the weight ratio of a):b) is for example between 3:1 and 1:12, especially 2.5:1 and 1:6, and more preferably 2:1 to 1:3.

Where component b) is a dithiocarbamate fungicide, the weight ratio of a):b) is for example between 1:3 and 1:120, especially 1:4 and 1:60, and more preferably 1:7 and 1:25.

Where component b) is a copper compound fungicide, the weight ratio of a):b) is for example between 1:1.5 and 1:100, especially 1:2 and 1:50, and more preferably 1:5 and 1:30.

Where component b) is a sulfur fungicide, the weight ratio of a):b) is for example between 1:6 and 1:400, especially 1:8 and 1:200, and more preferably 1:10 and 1:100.

Where component b) is a phthalimide fungicide of formula VIII, the weight ratio of a):b) is for example between 1:3 and 1:80, especially 1:4 and 1:40, and more preferably 1:8 and 1:20.

Where component b) is the compound of formula IX, the weight ratio of a):b) is for example between 1:2 and 1:25, especially 1:4 and 1:12, and more preferably 1:5 and 1:8.

Where component b) is the compound of formula X, the weight ratio of a):b) is for example between 3:1 and 1:16, especially 2.5:1 and 1:8, and more preferably 1:1 and 1:4.

Where component b) is the compound of formula XI, the weight ratio of a):b) is for example between 8:1 and 1:4, especially 2.5:1 and 1:2, and more preferably 2:1 and 1:1.

Where component b) is the compound of formula XII, the weight ratio of a) b) is for example between 6:1 and 1:2, especially 6:1 and 2:1, and more preferably 5:1 and 2:1.

Where component b) is the compound of formula XIII, the weight ratio of a):b) is for example between 1:3 and 1:40, especially 1:4 and 1:20, and more preferably 1:5 and 1:10.

Where component b) is the compound of formula XIV, the weight ratio of a):b) is for example between 3:1 and 1:8, especially 2.5:1 and 1:4, and more preferably 2:1 and 1:2.

Where component b) is the compound of formula XV, the weight ratio of a):b) is for example between 1.5:1 and 1:12, especially 1:1 and 1:6, and more preferably 1:1 and 1:4.

Where component b) is the compound of formula XVI, the weight ratio of a):b) is for example between 1.5:1 and 1:10, especially 1:1 and 1:5, and more preferably 1:1 and 1:3.

Where component b) is the compound of formula XVII, the weight ratio of a) b) is for example between 2:1 and 1:30, especially 1.5:1 and 1:15, and more preferably 1:1 and 1:5.

Where component b) is the compound of formula XVIII, the weight ratio of a):b) is for example between 8:1 and 1:4, especially 2.5:1 and 1:2, and more preferably 2:1 and 1:1.

Where component b) is the compound of formula XIX, the weight ratio of a):b) is for example between 1.5:1 and 1:12, especially 1:1 and 1:6, and more preferably 1:1 and 1:4.

Where component b) is the compound of formula XX, the weight ratio of a):b) is for example between 1:3 and 1:80, especially 1:4 and 1:40 and more preferably 1:1 and 1:25.

Where component b) is the compound of formula XXI, the weight ratio of a):b) is for example between 2:1 and 1:5, especially 1.5:1 and 1:2.5, and more preferably 1:1 and 1:2.

Where component b) is the compound of formula XXII, the weight ratio of a):b) is for example between 1:2 and 1:30, especially 1:3 and 1:15, and more preferably 1:3 and 1:10.

Where component b) is the compound of formula XXIII, the weight ratio of a):b) is for example between 1:2.5 and 1:30, especially 1:3 and 1:15, and more preferably 1:3 and 1:10.

Where component b) is the compound of formula XXIV, the weight ratio of a):b) is for example between 1.5:1 and 1:10, especially 1:1 and 1:5, and more preferably 1:2 and 1:4.

Where component b) is the compound of formula XXV, the weight ratio of a):b) is for example between 40:1 and 1:10, especially 20:1 and 1:5, and more preferably 10:1 and 1:2.

Where component b) is the compound of formula XXVI, the weight ratio of a):b) is for example between 1:1 and 1:10, especially 1:1 and 1:5, and more preferably 1:1 and 1:2.

Where component b) is the compound of formula XXVII, the weight ratio of a):b) is for example between 10:1 and 100:1, especially 5:1 and 50:1, and more preferably 2:1 and 20:1.

Where component b) is the compound of formula XXVIII, the weight ratio of a):b) is for example between 5:1 and 1:4, especially 3:1 and 1:2, and more preferably 2:1 and 1:1.

The method of the invention comprises applying to the plants to be treated or the locus thereof in admixture or separately, a fungicidally effective aggregate amount of a compound of formula I and a compound of component b).

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds. The novel combinations are extremely effective on a broad spectrum of phytopathogenic fungi, in particular from the Ascomycetes and Basidiomycetes classes. Some of them have a systemic action and can be used as foliar and soil fungicides.

The fungicidal combinations are of particular interest for controlling a large number of fungi in various crops or their seeds, especially wheat, rye, barley, oats, rice, maize, lawns, cotton, soybeans, coffee, sugarcane, fruit and ornamentals in horticulture and viticulture, and in vegetables such as cucumbers, beans and cucurbits.

The combinations are applied by treating the fungi or the seeds, plants or materials threatened by fungus attack, or the soil with a fungicidally effective amount of the active ingredients.

The agents may be applied before or after infection of the materials, plants or seeds by the fungi.

The novel combinations are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

Puccinia species in cereals,

Rhizoctonia species in cotton, rice and lawns,

Ustilago species in cereals and sugarcane,

*Venturia inaequalis* (scab) in apples,

*Helminthosporium* species in cereals,

*Septoria nodorum* in wheat,

*Septoria tritici* in wheat wheat,

*Rhynchosporium secalis* on barley,

*Pseudocercosporella herpotrichoides* in wheat and barley,

*Pyricularia oryzae* in rice,

*Phytophthora infestans* in potatoes and tomatoes,

Fusarium and Verticillium species in various plants,

*Plasmopara viticola* in grapes,

*Alternaria species* in fruit and vegetables.

When applied to the plants the compound of formula I is applied at a rate of 25 to 150 g/ha, particularly 50 to 125 g/ha, e.g. 75, 100, or 125 g/ha, in association with 20 to 3000 g/ha, particularly 20 to 2000 g/ha, e.g. 20. g/ha, 30 g/ha, 40 g/ha, 75 g/ha, 80 g/ha, 100 g/ha, 125 g/ha, 150 g/ha, 175 g/ha, 200 g/ha, 300 g/ha, 500 g/ha, 1000 g/ha, 1200 g/ha, 1500 g/ha, 2000 g/ha, or in some cases like sulfur up to 10000 g/ha of a compound of component b), depending on the class of chemical employed as component b).

Where the component b) is an anilinopyrimidine of formula II for example 300 to 900 g a.i./ha is applied in association with the compound of formula I. Where the component b) is an azole fungicide of formula III for example 20 to 350 g a.i./ha is applied in association with the compound of formula I. Where the component b) is an morpholine of formula IV for example 300 to 750 g a.i./ha is applied in association with the compound of formula I. Where the component b) is a strobilurin of formula V for example 75 to 250 g a.i./ha is applied in association with the compound of formula I. Where the component b) is a pyrrole of formula VI for example 200 to 750 g a.i./ha is applied in association with the compound of formula I. Where the component b) is a phenylamide of formula VII for example 50 to 300 g a.i./ha is applied in association with the compound of formula I. Where the component b) is a dithiocarbamate for example 500 to 3000 g a.i./ha is applied in association with the compound of formula I. Where the component b) is a copper compound for example 250 to 2500 g a.i. is applied in association with the compound of formula I. Where the component b) is sulfur for example 1000 to 10000 g a.i. is applied in association with the compound of formula I. Where the component b) is a phthalimide of formula VII for example 500 to 2000 g a.i./ha is applied in association with the compound of formula I. Where the component b) is the compound of formula IX for example 400 to 600 g a.i./ha is applied in association with the compound of formula I. Where the component b) is the compound of formula X for example 50 to 400 g a.i./ha is applied in association with the compound of formula I. Where the component b) is the compound of formula XI for example 20 to 100 g a.i./ha is applied in association with the compound of formula I. Where the component b) is the compound of formula XII for example 20 to 40 g a.i./ha is applied in association with the compound of formula I. Where the component b) is the compound of formula XIII for example 500 to 1000 g a.i./ha is applied in association with the compound of formula I. Where the component b) is the compound of formula XIV for example 50 to 200 g a.i./ha is applied in association with the compound of formula I. Where the component b) is the compound of formula XV for example 100 to 300 g a.i./ha is applied in association with the compound of formula I. Where the component b) is the compound of formula XVI for example 125 to 250 g a.i./ha is applied in association with the compound of formula I. Where the component b) is the compound of formula XVII for example 100 to 750 g a.i./ha is applied in association with the compound of formula I. Where the component b) is the compound of formula XVIII for example 20 to 100 g a.i./ha is applied in association with the compound of formula I. Where the component b) is the compound of formula XIX for example 100 to 300 g a.i./ha is applied in association with the compound of formula I. Where the component b) is the compound of formula XX for example 500 to 2000 g a.i./ha is applied in association with the compound of formula I. Where the component b) is the compound of formula XXI for example 75 to 125 g a.i./ha is applied in association with the compound of formula i. Where the component b) is the compound of formula XXII for example 300 to 750 g a.i./ha is applied in association with the compound of formula I. Where the component b) is the compound of formula XXIII for example 375 to 750 g a.i./ha is applied in association with the compound of formula I. Where the component b) is the compound of formula XXIV for example 125 to 250 g a.i./ha is applied in association with the compound of formula I. Where the component b) is the compound of formula XXV for example 5 to 200 g a.i./100 kg is applied for seed dressing in association with the compound of formula I. Where the component b) is the compound of formula XXVI for example 200 g a.i./100 kg is applied for seed dressing in association with the compound of formula I. Where the component b) is the compound of formula XXVII for example 2 g a.i./100 kg is applied for seed dressing in association with the compound of formula I. Where the component b) is the compound of formula XXVIII for example 40 to 80 g a.i./100 kg is applied for seed dressing in association with the compound of formula I.

In agricultural practice the application rates of the combination depend on the type of effect desired, and range from 0.02 to 4 kg of active ingredient per hectare.

When the active ingredients are used for treating seed, rates of 0.001 to 50 g a.i. per kg, and preferably from 0.01 to 10 g per kg of seed are generally sufficient.

The invention also provides fungicidal compositions comprising a compound of formula I and a compound of component b).

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants).

The term diluent as used herein means any liquid or solid agriculturally acceptable material including carriers which may be added to the active constituents to bring them in an easier or improved applicable form, respectively, to a usable or desirable strength of activity. Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water. The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable non-absorbent carriers are, for example, calcite or sand. In addition, a great number of materials of inorganic or organic nature can be used, e.g. especially dolomite or pulverised plant residues. Depending upon the nature of the compounds of formula I and component b) to be formulated, suitable surface-active compounds are non-ionic, cationic and/or anionic surnactants having good emulsifying, dispersing and wetting properties. The term "surfactants" will also be understood as comprising mixtures of surfactants. Particularly advantageous application-promoting adjuvants are also natural or synthetic phospholipids of the cephalin and lecithin series, e.g. phosphatidylethanolamine, phosphatidylserine, phosphatidylglycerol and lysolecithin.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least the compound of formula I together with a compound of component b), and optionally other active agents, particularly microbides or conservatives or the like.

Concentrate forms of compositions generally contain in between about 2 and 80%, preferably between about 5 and 70% by weight of active agent. Application forms of formulation may for example contain from 0.01 to 20% by weight, preferably from 0.01 to 5% by weight of active agent.

The Examples which follow serve to illustrate the invention, "active ingredient" denoting a mixture of compound I and a compound of component b) in a specific mixing ratio.

Formulations may be prepared analogously to those described in, for example, WO 97/33890.

SLOW RELEASE CAPSULE SUSPENSION 28 parts of a combination of the compound of formula I and a compound of component b), or of each of these compounds separately, are mixed with 2 parts of an aromatic solvent and 7 parts of toluene diisocyanatete/polymethylenepolyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerisation reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns. The resulting formulation is applied to seeds as an aqueous suspension in an apparatus suitable for that purpose.

SEED DRESSING FORMULATION 25 parts of a combination of compounds of formulae I and II, 15 parts of dialkylphenoxypoly(ethylenoxy)ethanoi, 15 parts of fine silica, 44 parts of fine kaolin, 0.5 parts of Rhodamine B as a colirant and 0.5 parts of Xanthan Gum are mixed and ground in a contraplex mill at approx. 10000 rpm to an average particle size of below 20 microns. The resulting formulation is applied to the seeds as an aqueous suspension in an apparatus suitable for that purpose.

Whereas commercial products will preferably be formulated as concentrates, the end user will normally employ dilute formulations.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20–22; 1967):

ppm=milligrams of active ingredient (=a.i.) per litre of spray mixture

X=% action by active ingredient I using p ppm of active ingredient

Y=% action by active ingredient II using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect. Alternatively the synergistic action may also be determined from the dose response curves according to the soiled WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations (EC $90_{observed}$). The thus experimentally found values of the mixtures at a given weight ratio are compared with the values that would have been found were only a complementary efficacy of the components was present (EC 90 (A+B)$_{expected}$). The EC90 (A+B)$_{expected}$ is calculated according to Wadley (Levi et al., EPPO- Bulletin 16, 1986, 651–657):

$$EC90 \ (A + B)_{expected} = \frac{a+b}{\frac{a}{EC90 \ (A)_{observed}} + \frac{b}{EC90 \ (B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC90 (A+B)$_{expected}$/EC90 (A+B)$_{observed}$ expresses the factor of interaction (F). In case of synergism, F is >1.

EXAMPLE B-1

Efficacy against *Erysiphe graminis* f.sg. tritici on wheat

Wheat plants c.v. "Arina", about 10 days old, are sprayed with aqueous suspensions of the active ingredients or mixtures thereof. One day later, the plants are inoculated by dusting with spores of *Erysiphe graminis*. The tests may also be carried out with curative applications, i.e. application 1–3 days after artificial inoculation of the plants. The plants are incubated in the greenhouse or in climate chambers at 20° C., 70% relative humidity. 7 to 10 days after inoculation, fungal attack on primary leaves is assessed.

Results:

TABLE 1

Mixture I.01 + fludioxonil (compound VI wherein $R_{15}$ and $R_{16}$ together form a bridge —$OCF_2$—O—)

| cmpd I.01 ppm | Fludioxonil ppm | Ratio | % activity observed | % activity expected | Colby's factor |
|---|---|---|---|---|---|
| — | — | — |  |  |  |
| 10 |  |  | 0 |  |  |
| 25 |  |  | 0 |  |  |
| 50 |  |  | 12 |  |  |
| 100 |  |  | 26 |  |  |
| 250 |  |  | 34 |  |  |
| 500 |  |  | 66 |  |  |
|  | 10 |  | 2 |  |  |
|  | 25 |  | 0 |  |  |
|  | 50 |  | 6 |  |  |
|  | 100 |  | 14 |  |  |
|  | 250 |  | 19 |  |  |
|  | 500 |  | 27 |  |  |
| 10 | 10 | 1:1 | 21 | 2 | 13.7 |
| 10 | 25 | 1:2,5 | 27 | 0 | — |
| 10 | 50 | 1:5 | 11 | 6 | 1.8 |
| 10 | 100 | 1:10 | 30 | 14 | 2.2 |
| 10 | 250 | 1:25 | 19 | 19 | 1.0 |
| 25 | 25 | 1:1 | 13 | 0 | — |
| 25 | 50 | 1:2 | 31 | 6 | 4.9 |
| 25 | 100 | 1:4 | 50 | 14 | 3.6 |
| 25 | 250 | 1:10 | 23 | 19 | 1.2 |
| 25 | 500 | 1:20 | 46 | 27 | 1.7 |
| 50 | 50 | 1:1 | 39 | 17 | 2.3 |
| 50 | 100 | 1:2 | 56 | 24 | 2.3 |
| 50 | 250 | 1:5 | 39 | 29 | 1.4 |
| 50 | 500 | 1:10 | 72 | 36 | 2.0 |
| 100 | 100 | 1:1 | 62 | 36 | 1.7 |
| 100 | 250 | 1:2,5 | 70 | 41 | 1.7 |
| 100 | 500 | 1:5 | 63 | 46 | 1.4 |
| 250 | 250 | 1:1 | 75 | 47 | 1.6 |
| 250 | 500 | 1:2 | 81 | 52 | 1.6 |
| 500 | 500 | 1:1 | 93 | 73 | 1.3 |

TABLE 2

Mixture I.01 + cyproconazole (compound III wherein $R_5$ is Cl, $R_6$ and $R_7$ are H, $R_8$ is $CH_3$, $R_9$ is cyclopropyl and A is a moiety (j))

| cmpd. I.01 ppm | cyproconazole ppm | Ratio | % activity observed | % activity expected | Colby's factor |
|---|---|---|---|---|---|
| — | — |  | 0 (control) |  |  |
| 0.5 |  |  | 0 |  |  |
| 1 |  |  | 0 |  |  |
| 2.5 |  |  | 0 |  |  |
| 5 |  |  | 8 |  |  |
| 10 |  |  | 8 |  |  |
|  | 1 |  | 8 |  |  |
|  | 2.5 |  | 49 |  |  |
|  | 5 |  | 100 |  |  |
|  | 10 |  | 100 |  |  |
| 0.5 | 1 | 1:2 | 18 | 8 | 2.4 |
| 0.5 | 2.5 | 1:5 | 69 | 49 | 1.4 |
| 0.5 | 5 | 1:10 | 100 | 100 | 1.0 |
| 1 | 1 | 1:1 | 23 | 8 | 3.0 |
| 1 | 2.5 | 1:2.5 | 92 | 49 | 1.9 |
| 1 | 5 | 1:5 | 100 | 100 | 1.0 |
| 2.5 | 1 | 2.5:1 | 38 | 8 | 5.0 |
| 2.5 | 2.5 | 1:1 | 74 | 49 | 1.5 |
| 2.5 | 5 | 1:2 | 100 | 100 | 1.0 |
| 5 | 1 | 5:1 | 43 | 15 | 2.9 |
| 5 | 2.5 | 2:1 | 92 | 53 | 1.7 |
| 5 | 5 | 1:1 | 100 | 100 | 1.0 |
| 10 | 2.5 | 4:1 | 98 | 53 | 1.9 |

TABLE 3

Mixture I.01 + propiconazole (compound III wherein $R_5$ and $R_6$ are Cl, $R_7$ and $R_8$ are H, $R_9$ is propyl and A is the moiety (ii))

| cmpd. I.01 ppm | propiconazole ppm | Ratio | % activity observed | % activity expected | Colby's factor |
|---|---|---|---|---|---|
| — | — | | 0 (control) | | |
| 0.5 | | | 2 | | |
| 1 | | | 0 | | |
| 2.5 | | | 14 | | |
| 5 | | | 8 | | |
| 10 | | | 4 | | |
| | 0.1 | | 0 | | |
| | 0.25 | | 0 | | |
| | 0.5 | | 6 | | |
| | 1 | | 8 | | |
| | 2.5 | | 72 | | |
| 0.5 | 0.1 | 5:1 | 18 | 2 | 7.7 |
| 0.5 | 0.25 | 2:1 | 19 | 2 | 8.2 |
| 0.5 | 0.5 | 1: | 23 | 8 | 2.8 |
| 0.5 | 1 | 1:2 | 51 | 11 | 4.8 |
| 0.5 | 2.5 | 1:5 | 90 | 73 | 1.2 |
| 1 | 0.5 | 2:1 | 25 | 6 | 4.2 |
| 1 | 1 | 1:1 | 42 | 8 | 5.0 |
| 1 | 2.5 | 1:2.5 | 87 | 72 | 1.2 |
| 1 | 5 | 1:5 | 99 | 99 | 1.0 |
| 2.5 | 0.5 | 5:1 | 42 | 19 | 2.2 |
| 2.5 | 1 | 2.5:1 | 57 | 22 | 2.6 |
| 2.5 | 2.5 | 1:1 | 94 | 76 | 1.2 |
| 5 | 1 | 5:1 | 61 | 16 | 3.8 |
| 5 | 2.5 | 2:1 | 90 | 75 | 1.2 |
| 5 | 5 | 1:1 | 99 | 99 | 1.0 |
| 10 | 2.5 | 4:1 | 92 | 73 | 1.2 |

TABLE 4

Mixture I.01 + fenpropidine (compound XXII)

| cmpd I.01 ppm | fenpropidine ppm | Ratio | % activity observed | % activity expected | Colby's factor |
|---|---|---|---|---|---|
| — | — | | 0 (control) | | |
| 0.25 | | | 0 | | |
| 0.5 | | | 0 | | |
| 1 | | | 0 | | |
| 2.5 | | | 0 | | |
| | 2.5 | | 35 | | |
| | 5 | | 51 | | |
| | 10 | | 63 | | |
| 0.25 | 5 | 1:20 | 63 | 51 | 1.2 |
| 0.5 | 5 | 1:10 | 59 | 51 | 1.2 |
| 0.5 | 10 | 1:20 | 88 | 63 | 1.4 |
| 1 | 5 | 1:4 | 59 | 51 | 1.2 |
| 2.5 | 10 | 1:4 | 80 | 63 | 1.3 |

EXAMPLE B-2

Efficacy against *Erysiphe graminis* f.sp. hordei on barley a) Protective or Curative Activity Barley plants c.v. "Golden Promise" are used. The testing procedure is the same as described in Example B-1.

b) Systemic Activity

Aqueous spray mixtures of the active ingredients or mixtures thereof are poured next to barley plants approximately 8 cm high. Care is taken that the spray mixture does not come into contact with the aerial parts of the plants. 48 hours later, the plants are dusted with conidia of the fungus. The infected plants are placed in a greenhouse at 22° C. The disease attack on the foliage is assessed 12 days after the infection.

EXAMPLE B-3

Activity Against *Podosophaera leucotricha* on Apples

Apple seedlings with about 10 cm long fresh shoots are sprayed with aqueous spray mixtures of the active ingredients or the mixtures thereof. The treated plants are inoculated 24 hours later with a conidia suspension of the fungus and placed in a climatic chamber at 70% relative humidity and 20° C. The test may also be carried out with curative application 2 days after inoculation. Disease attack is evaluated 12–14 days after inoculation.

EXAMPLE B-4

Activity Against *Uncinula necator* on Grapes

Grape plants grown from seeds (c.v. "Gutedel"), at the 4–5 leaves stage, are sprayed with aqueous spray mixtures of the active ingredients or the mixtures thereof. One day later, the treated plants are inoculated with a spore suspension of Uncinula necator and then incubated in the growth chamber at +24° C. and 70% relative humidity. The test may also be carried out using curative application 2 days after inoculation. Disease attack is evaluated 14 days after inoculation.

EXAMPLE B-5

Activity Against *Sphaerotheca fuliginea* on Cucumbers

Cucumber seedlings c.v. "chinesische Schlange", about 2 weeks old (cotyledon stage), are sprayed with aqueous spray mixtures of the active ingredients or the mixtures thereof. One day later, the treated plants are inoculated with a spore suspension of Sphaerotheca fuliginea and then incubated in a growth chamber at +24° C. and 70% relative humidity. The test may also be carried out using curative application 2 days after inoculation. Disease attack is evaluated 10 days after inoculation.

EXAMPLE B-6

Activity Against *Venturia inaequalis* on Apples

Apple seedlings with about 10 cm long fresh shoots are sprayed with aqueous spray mixtures of the active ingredients or the mixtures thereof. The treated plants are inoculated 24 hours later with a conidia suspension of the fungus. The plants are incubated for 2 days at +20° C. and 95–100% relative humidity, then further 10 days in the greenhouse at 20–24° C. and 80% relative humidity. Disease attack is evaluated on the youngest treated leaves.

Example B-7

Activity Against *Puccinia recondita* in Wheat

Wheat plants c.v. "Arina", about 10 days old, are sprayed with aqueous suspensions of the active ingredients or mixtures thereof. One day later, the plants are inoculated with a spore suspension of the fungus. The test may also be carried out with curative applications, i.e. application 1–3 days later after artificial inoculation of the plants. The plants are incubated in a growth chamber for 2 days at ° 20° C. and 95–100% relative humidity, then further 10 days at 20° C. and 70% relative humidity. Fungal attack on primary leaves is assessed.

TABLE 5

Mixture I.01 + cmpd. V wherein X is O, Y is N and $R_{14}$ is 4-(3-trifluoromethylphenyl) 3-aza-2-oxa-3-pentyl.

| cmpd. I.01 ppm | cmpd. V ppm | Ratio | % activity observed | % activity expected | Colby's factor |
|---|---|---|---|---|---|
| — | — | | 0 (control) | | |
| 0.5 | | | 0 | | |
| 1 | | | 0 | | |
| 2.5 | | | 0 | | |
| 5 | | | 0 | | |
| 10 | | | 0 | | |
| 25 | | | 0 | | |
| | 1 | | 17 | | |
| | 2.5 | | 32 | | |
| | 5 | | 38 | | |
| | 10 | | 37 | | |
| 0.5 | 2.5 | 1:5 | 58 | 32 | 1.8 |
| 0.5 | 5 | 1:10 | 45 | 38 | 1.2 |
| 1 | 2.5 | 1:2.5 | 53 | 32 | 1.6 |
| 1 | 5 | 1:1 | 52 | 38 | 1.4 |
| 1 | 10 | 1:10 | 74 | 37 | 2.0 |
| 2.5 | 1 | 2.5:1 | 43 | 17 | 2.6 |
| 2.5 | 2.5 | 1:1 | 46 | 32 | 1.4 |
| 2.5 | 5 | 1:2 | 45 | 38 | 1.2 |
| 2.5 | 10 | 1:4 | 70 | 37 | 1.9 |
| 5 | 2.5 | 2:1 | 52 | 32 | 1.6 |
| 5 | 5 | 1:1 | 47 | 38 | 1.4 |
| 5 | 10 | 1:2 | 76 | 37 | 2.1 |
| 10 | 5 | 2:1 | 59 | 38 | 1.6 |
| 10 | 10 | 1:1 | 79 | 37 | 2.1 |
| 25 | 10 | 2.5:1 | 68 | 37 | 1.9 |

EXAMPLE B-8

Activity Against *Septoria nodorum* in Wheat

Wheat plants c.v. "Zenith", about 10 days old, are sprayed with aqueous suspensions of the active ingredients or mixtures thereof. One day later, the plants are inoculated with a spore suspension of the fungus. The tests may also be carried out with curative timings, i.e. application 1–3 days after artificial inoculation of the plants. The plants are subsequently incubated in a growth chamber at a relative atmospheric humidity of 95–100%. Disease attack is assessed 10 days after the inoculation.

EXAMPLE B-9

Activity Against *Plasmopara viticola* in Grapevines

Grape plants grown from seeds /c.v. "Gutedel"), at the 4-to-5-leaf stage, are sprayed with aqueous spray mixtures of the active ingredients or the mixtures thereof. One day later, the treated plants are inoculated with a spore suspension of the fungus. The plants are incubated in a growth chamber 2 days at +22° C. and relative humidity of 95 to 100%, then 4 days at 22° C. and 70% relative humidity, followed again by 1 day at high humidity to induce sporulation. Disease attack is evaluated 7 days after inoculation.

EXAMPLE B-10

Activity Against *Phytophthora infestans* in Tomatoes

Tomato plants cv. "Baby", about 4 weeks old, are sprayed with aqueous spray mixtures of the active ingredients or the mixtures thereof. One day later, the treated plants are inoculated with a zoospore suspension of the fungus. The plants are incubated for 6 days in moisture chambers at 18° C. and 100% relative humidity. After this period, disease attack is evaluated.

The efficacy of the test combinations and the single active ingredients in the above tests is determined by comparing the degree of fungal attack with that on untreated, similarly inoculated check plants.

EXAMPLE B-11

Activity Against *Gerlachia nivalis* on Wheat

Wheat seed which is infected with *G.nivalis* is harvested from the field. This seed is treated with one of the active ingredients I or b) or with mixtures of the active ingredients. The active components are first dispersed in water and this dispersion is then sprayed onto the seed which is on a rotating disc. This procedure corresponds to conditions found in practice. Untreated seeds from the same origin are used for comparison purposes. Batches of 100 grains are sown in seed trays (45×35×10 cm) in sterile soil at a depth of 2 cm. Three replicates of the test are run. The seed trays are kept moist for 21 days at 5° C. with the exclusion of light. They are then transferred to a control-environment cabinet with illumination (day/night: 16/8 hours; 10° C.) where emergence takes place. Germination does not take place in the case of those grains which are heavily infected with *G.nivalis*. After 10 days, the trays are covered with a plastic film and maintained at 100C without light. Due to the high atmospheric humidity under the cover, fungal mycelium becomes apparent on the stem base of those plants which are infected with *G.nivalis*. About 60 days after sowing, the number of existing plants and the number of infected plants are determined. The sum of the number of non-germinated grains and the number of infected plants forms the total infection rate. This rate is compared with the total infection rate in the comparison seed trays with untreated seeds and expressed as the total percentage infection rate.

EXAMPLE B-12

Activity Against *Helminthosporium gramineum* on Barley

Barley seed which is infected with *H.gramineum* is harvested from the field. This seed is treated with one of the active ingredients I or b) or with mixtures of the active ingredients. The active components are first dispersed in water and this dispersion is then sprayed onto the seed which is on a rotating disc. This procedure corresponds to conditions found in practice. Untreated seeds from the same origin are used for comparison purposes. Batches of 100 grains are sown in seed trays (45×35×10 cm) in sterile soil at a depth of 2 cm. Three replicates of the test are run. The seed trays are kept moist for 28 days at 2° C. with the exclusion of light. They are then transferred to a greenhouse (day/night: 18/12° C.). About 60 days after sowing, the number of existing plants and the number of infected plants are determined. Symptoms are expressed as typical stripe-shaped spots on the first leaf. The total infection rate is compared with the total infection rate in the comparison seed trays with untreated seeds and expressed as the total percentage infection rate.

TABLE 6

Mixture I.01 + triticonazole (compound III wherein $R_5$ is Cl, $R_6$ is H and A the moiety (iv)).

| cmpd. I.01 g a.i./100 kg seed | triticonazole g a.i./100 kg seed | Ratio | % activity observed | % activity expected | Colby's factor |
|---|---|---|---|---|---|
| — | — | | 0 (control) | | |
| 20 | | | 11 | | |
| | 20 | | 12 | | |
| | 40 | | 22 | | |
| 20 | 40 | 1:2 | 36 | 31 | 1.2 |
| 20 | 20 | 1:1 | 29 | 22 | 1.3 |

EXAMPLE B-13

Activity Against *Septoria nodorum* on Wheat

Wheat seed which is infected with *S.nodorum* is harvested from the field. This seed is treated with one of the active ingredients I or b) or with mixtures of the active ingredients. The active components are first dispersed in water and this dispersion is then sprayed onto the seed which is on a rotating disc. This procedure corresponds to conditions found in practice. Untreated seeds from the same origin are used for comparison purposes. The testing method used is based on that published by Holmes and Colhoun (Ann. of appl. Biolg., 1973, 225–232). Batches of 100 grains are sown in seed trays (45×35×10 cm) in sterile soil at a depth of 2 cm. Three replicates of the test are run. The seed trays are kept moist for 14 days at 8–10° C. with the exclusion of light. They are then transferred to a greenhouse (20° C.) for a period of another 14 days. After that, the seedlings are taken out of the soil and washed with water before infection is assessed. The total infection rate is compared with the total infection rate in the comparison seed trays with untreated seeds and expressed as the total percentage infection rate.

EXAMPLE B-14

Activity Against *Erysiphe graminis* on Barley or Wheat

Cereal seed is treated with one of the active ingredients I or b) or with mixtures of the active ingredients. The active components are first dispersed in water and this dispersion is then sprayed onto the seed which is on a rotating disc. This procedure corresponds to conditions found in practice. Untreated seeds from the same origin are used for comparison purposes. Batches of 100 grains are sown in seed trays (45×35×10 cm) in sterile soil at a depth of 2 cm. Three replicates of the test are run. The seeds emerge at controlled conditions (day/night: 15/10° C.). In the stage of 2–3 emerged leaves, the plants are artificially inoculated by shaking heavily infected plants over the test trays. The seed trays are then kept at elevated temperatures (day/night: 22/18° C.). Assessments of the percentage infected leaf area are done at regular intervals. The total infection rate is compared with the total infection rate in the comparison seed trays with untreated seeds and expressed as the total percentage infection rate.

The mixtures according to the invention exhibit good activity in these Examples.

What is claimed is:

1. A method of combating phytopathogenic diseases on crop plants which comprises applying to the crop plants, seeds or the locus thereof being infested with said phytopathogenic disease an effective amount of a) a thieno[2,3-d]pyrimidin-4-one derivative of formula I

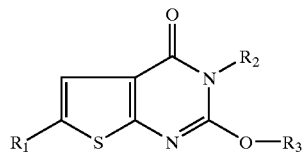

(I)

wherein
$R_1$ is halogen,
$R_2$ is $C_1$–$C_5$alkyl, —$CH_2$-cyclopropyl and
$R_3$ is $C_1$–$C_5$alkyl, —$CH_2$-cyclopropyl;
in association with an amount of b) pyrrole compound of the formula VI

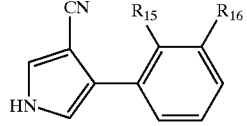

(VI)

wherein
$R_{15}$ and $R_{16}$ are indendently halo, or together from a perhalomethylendioxo bridge;
which synergistically enhances the activity against phytopathogenic diseases.

2. A method according to claim 1 wherein the component a) comprises a compound of the formula I wherein $R_1$ is chloro or bromo, $R_2$ is n-propyl, n-butyl, or i-butyl and $R_3$ is n-propyl, n-butyl or i-butyl.

3. A method according to claim 1 wherein the component b) is selected from the group consisting of fenpiclonil and fludioxonil.

4. A fungicidal composition comprising a fungicidally effective combination of component a) and component b) as defined in claim 1, wherein the components are present in amounts which synergistically enhances the activity against phytopathogenic diseases.

5. A composition according to claim 4 wherein the weight ratio of a) to b) is between 100:1 and 1:400.

6. A composition according to claim 4 wherein the component a) comprises a compound of the formula I wherein $R_1$ is chloro or bromo, $R_2$ is n-propyl, n-butyl or i-butyl and $R_3$ is n-propyl, n-butyl or i-butyl.

7. A composition according to claim 5 wherein the component b) is selected from the group consisting of fenpiclonil and fludioxonil.

* * * * *